United States Patent [19]

Kahl et al.

[11] Patent Number: 5,200,560

[45] Date of Patent: * Apr. 6, 1993

[54] PREPARATION OF CARBOXYLIC CHLORIDES

[75] Inventors: Thomas M. Kahl, Roemerberg; Jochem Henkelmann, Ludwigshafen; Leopold Hupfer, Friedelsheim; Wolfgang Franzischka, Frankenthal; Wolfgang Schwarz, Otterstadt, all of Fed. Rep. of Germany

[73] Assignee: BASF Aktiengesellschaft, Ludwigshafen, Fed. Rep. of Germany

[ * ] Notice: The portion of the term of this patent subsequent to Nov. 24, 2009 has been disclaimed.

[21] Appl. No.: 908,439

[22] Filed: Jun. 30, 1992

Related U.S. Application Data

[63] Continuation of Ser. No. 686,817, Apr. 17, 1991, abandoned.

[30] Foreign Application Priority Data

Apr. 21, 1990 [DE] Fed. Rep. of Germany ....... 4012781

[51] Int. Cl.⁵ .............................................. C07L 51/58
[52] U.S. Cl. ..................................................... 562/857
[58] Field of Search ......................................... 562/857

[56] References Cited

U.S. PATENT DOCUMENTS

| 3,547,960 | 12/1970 | Hauser . |
| 3,857,841 | 12/1974 | Keil ..................... 544/406 |
| 4,880,576 | 11/1989 | Blank et al. ........................ 562/828 |

FOREIGN PATENT DOCUMENTS

| 2000442 | 4/1990 | Canada . |
| 31504 | 7/1981 | European Pat. Off. . |
| 0050779 | 5/1982 | European Pat. Off. . |
| 367050 | 5/1990 | European Pat. Off. . |
| 1931074 | 1/1970 | Fed. Rep. of Germany . |
| 2240883 | 2/1974 | Fed. Rep. of Germany . |
| 2950155 | 7/1981 | Fed. Rep. of Germany . |
| 3439937 | 5/1986 | Fed. Rep. of Germany . |
| 3836967 | 5/1990 | Fed. Rep. of Germany . |

OTHER PUBLICATIONS

Chemical Abstracts, vol. 69, Ref. 86395s, 1968.

Primary Examiner—Paul J. Killos
Attorney, Agent, or Firm—John H. Shurtleff

[57] ABSTRACT

A process for the preparation of a carboxylic chloride of the general formula I

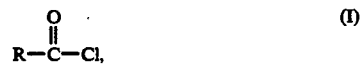

in which R denotes $C_1$–$C_{30}$-alkyl, $C_2$–$C_{30}$-alkenyl or $C_2$–$C_{30}$-alkynyl, from a carboxylic acid of the general formula II

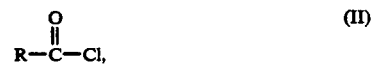

in which R has the meanings stated, and phosgene $COCl_2$ (III), in the presence of a catalyst adduct comprising phosgene and N,N-disubstituted formamide of the general formula IV

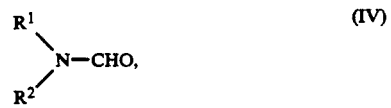

in which $R^1$ and $R^2$ are independently $C_1$–$C_3$-alkyl or $R^1$ and $R^2$ together form a $C_4$- or $C_5$-alkylene chain which may or may not be interrupted by an oxygen atom or by a nitrogen atom carrying a $C_1$–$C_3$-alkyl group or CHO, the product being isolated by phase separation, wherein the amount of phosgene added to the formamide (IV) is from 20 to 70% molar, based on the formamide.

13 Claims, No Drawings

PREPARATION OF CARBOXYLIC CHLORIDES

This application is a continuation of application Ser. No. 686,817, filed Apr. 17, 1991 now abandoned.

Carboxylic chlorides are readily produced by reacting appropriate carboxylic acids with phosgene. This reaction needs to be catalyzed, and the catalysts used are for example carboxamides, preferably N-alkyl formamides (DE-A 3,439,937).

In the case of N,N-dialkyl formamides, the size of the alkyl groups can vary from that in dimentyl formamide to those in formamides containing 30 carbon atoms (EP-A 0,050,779, DE-A 2,950,155, DE-A 1,931,074).

The choice of catalyst system has a decisive influence on the rate at which phosgenation of a carboxylic acid to a carboxylic chloride takes place and on the procedure to be adopted for working up the reaction mixture.

In some cases, distillation of the catalyst-containing product could be a conceivable alternative to filtration of such tarry crude products. However, the distillation of the acid chlorides obtained not only consumes time and energy but also suffers from a number of other drawbacks.

Many relatively long-chain acid chlorides cannot be distilled without partial decomposition. It is also known that decomposition of the catalyst present in the bottoms can contaminate the distilled products. The accumulation of large amounts of catalyst residues during distillation is hazardous on account of the risk of spontaneous thermal decomposition.

The activity of the catalyst is greatly reduced by the process of working up the contaminated product by both filtration and distillation techniques. In most cases, the catalyst becomes useless and cannot be recycled to the process.

Thus both the distillation and the filtration of catalyst-containing carboxylic chlorides are unsatisfactory purification methods. Due to the loss of catalyst incurred thereby, the amount of catalyst required must be minimized as far as possible.

In DE-A 2,950,155 diisobutyl formamide is used as catalyst, which is soluble in the reaction mixture during each phase of the reaction. If it has been decided to run the process without final distillation of the acid chloride, the amount of soluble catalyst in the product must be kept at a minimum for purity reasons. This catalyst system also precludes any re-use of the catalyst, since it is discharged with the product.

It is further known that reactions involving phosgene are more effective the greater the amount of catalyst. Conversely, small amounts of catalyst lead to poor utilization of the phosgene gas introduced or to long gassing periods.

DE-A 2,240,883 describes the manufacture of carboxylic chlorides using equimolar amounts of carboxylic acid and catalyst. However, to recover the large amount of catalyst it is necessary to effect separation thereof by adding a volume of benzene which is from 3 to 4 times the volume of the final reaction mixture and then distilling the resulting benzene solution.

JP 1,613/68 also describes the use of large amounts of catalyst for the manufacture of linoleic chloride using from 10 to 50% molar of dimethyl formamide or even from 1 to 10 equivalents of dimethyl formamide, based on the amount of linoleic acid used. The resulting acid chloride must be distilled and in some cases further purified by treatment with activated carbon. No provision is made for the re-use of this large amount of catalyst.

In the synthesis of carboxylic chlorides from carboxylic acids and phosgene there is the well-known problem concerning the removal of excess phosgene from the crude acid chloride.

According to the prior art, phosgene-containing carboxylic chloride can be freed from phosgene by stripping with nitrogen for several hours and/or by applying a slight vacuum. This procedure is time-consuming and lowers the space-time yield of the process considerably.

According to DE-A 2,950,155, the excess phosgene is distilled over with the first portion of distilled acid chloride. The use of this method can also involve a lowering of the space-time yield and, in addition, it calls for more equipment and more analytical tests.

DE-A 2,240,883 reveals a workup method in which the reaction solution is briefly washed with ice water prior to the distillation step. In view of the susceptibility of carboxylic chlorides to hydrolysis such a method presents problems for realization on an industrial scale.

The process revealed in JP 10,613/68 also must effect the removal of excess phosgene by distillation of the crude acid chloride.

DE-A 3,836,967 describes a method of manufacturing higher carboxylic chlorides, wherein the amount of phosgene added to the N,N-dialkyl formamide is 100% based on the formamide. This procedure leads to not inconsiderable losses of phosgene.

It is an object of the present invention to provide a process for the preparation of carboxylic chlorides which overcomes the aforementioned drawbacks.

Accordingly, we have found a novel, improved process for the preparation of a carboxylic chloride of the general formula I $$R-\overset{O}{\underset{\|}{C}}-Cl, \quad (I)$$

in which R denotes $C_1$-$C_{30}$-alkyl, $C_2$-$C_{30}$-alkenyl or $C_2$-$C_{30}$-alkynyl, from a carboxylic acid of the general formula II $$R-\overset{O}{\underset{\|}{C}}-OH, \quad (II)$$

in which R has the meanings stated, and phosgene $COCl_2$ (III), in the presence of a catalyst adduct comprising phosgene and N,N-disubstituted formamide of the general formula IV $$\begin{matrix} R^1 \\ \phantom{R^1}\diagdown \\ \phantom{R^1\diagdown}N-CHO, \\ \phantom{R^1}\diagup \\ R^2 \end{matrix} \quad (IV)$$

in which $R^1$ and $R^2$ are independently $C_1$-$C_3$-alkyl or $R^1$ and $R^2$ together form a $C_4$- or $C_5$-alkylene chain which may or may not be interrupted by an oxygen atom or by a nitrogen atom carrying a $C_1$-$C_3$-alkyl group or CHO, the product being isolated by phase separation, wherein the amount of phosgene added to the formamide (IV) is from 20 to 70% molar, based on the formamide.

The carboxylic chlorides (I) may be obtained as follows:

a) Batch method

To the reaction mixture comprising a carboxylic acid (II) and the adduct of phosgene and N,N-dialkyl formamide of formula (IV) there is added an amount of liquid or gaseous phosgene which is equivalent to the carboxylic acid (II). The time taken for the introduction of the phosgene can be limited to a few hours and the phosgene is converted virtually quantitatively. The mixture is then allowed to stand for from 1 to 2 hours before the phases are separated.

b) Continuous method (preferred)

A suitable reactor is, for example, a stirred vessel, a cascade of stirred vessels or a countercurrent column.

If a stirred vessel is used, the carboxylic acid (II) and the adduct of phosgene and N,N-disubstituted formamide of formula (IV) are initially placed in the vessel, and liquid or gaseous phosgene is added. After an amount of phosgene which is equivalent to the carboxylic acid (II) has been introduced, concurrent feeds of carboxylic acid (II), adduct of phosgene and N,N-disubstituted formamide, and phosgene (in a substantially equimolar amount based on the carboxylic acid) are let into the vessel.

The reaction mixture is removed through a vertical outlet at the same rate as the reactants are introduced and is then passed to a separator basin, from which the desired product (I) forming the top phase can be continuously removed, while the adduct of phosgene and N,N-disubstituted formamide forming the bottom phase can be continuously recycled to the reactor. In order to keep the content of phosgene in the catalyst as constant as possible throughout the process, it is important to make up for phosgene losses, caused by entrainment of phosgene by the off-gases, by an appropriately increased rate of phosgene flow.

The temperature used for the reaction of carboxylic acid (II) with the adduct of phosgene (III) and N,N-disubstituted formamide (IV), carried out batchwise or, preferably, continuously is between 20° and 100° C., preferably between 30° and 80° C. and more preferably between 40° and 70° C.

For this reaction the amount of the adduct of phosgene and N,N-disubstituted formamide used is from 5 to 200% molar, preferably from 10 to 100% molar and more preferably from 10 to 30% molar, based on the carboxylic acid used.

The amount of phosgene adsorbed on the catalyst is from 20 to 70% molar, preferably from 30 to 60% molar and more preferably from 40 to 50% molar, based on formamide moiety.

The phosgene content of the catalyst can be continuously determined by measuring the density, viscosity, conductivity or chloride-content of the heavier phase separating in the separator.

Phase separation is carried out at a temperature of from −15° to 40° C., preferably from −10° to 30° C. and more preferably from −5° to 20° C.

The amount of phosgene (III) used is substantially equimolar to the carboxylic acid (II).

Since the off-gas from the reaction contains only insignificant amounts of phosgene (from 1.0 to 1.5%), in addition to carbon dioxide and hydrogen chloride, condensation of the phosgene is not necessary. The off-gases can be directly fed to the off-gas washing plant. Thus the off-gas need only be cooled to a temperature at which the resulting target product condenses as completely as possible.

In order to improve phase separation or convert solid acids, for example, it is possible to add an indifferent solvent to the reaction mixture, examples thereof being saturated aliphatic hydrocarbons, ethers, acetonitrile, benzene, toluene and cyclohexane.

The carboxylic chloride is obtained in high yield and purity. It is frequently possible to use it without further purification, but in some cases a simple distillation may be necessary where extremely pure products are required. The carboxylic chlorides produced by the reaction are free from phosgene and there is no necessity to carry out measures to dephosgenate the crude acid chloride.

The process of the invention for the preparation of acid chlorides from aliphatic carboxylic acids is particularly suitable for monocarboxylic acids, i.e. for the preparation of compounds of the general formula RCOX, where R is an aliphatic hydrocarbon group and X is chlorine. The said aliphatic group may be linear or branched, saturated, or ehtylenically or acetylenically unsaturated. Particularly preferred aliphatic carboxylic acids are those having from 1 to 30 carbon atoms and especially those having from 1 to 20 carbon atoms.

Suitable N,N-disubstituted formamides are dimethyl formamide, ethylmethyl formamide, methyl-n-propyl formamide, methylisopropyl formamide, diethyl formamide, ethyl-n-propyl formamide, ethyl-isopropyl formamide, di-n-propyl formamide, n-propylisopropyl formamide and di-isopropyl formamide. Diethyl formamide and, in particular, dimethyl formamide are preferred.

EXAMPLES 1 TO 8 Continuous Phosgenation

At a temperature of from 40° to 70° C., 1.0 mole/h of a carboxylic acid, 0.2 mole/h of adduct of phosgene and N,N-disubstituted formamide (phosgene content 50 to 60% molar, based on formamide), and 1.0 mole/h of phosgene are introduced to a main reactor (MR) having a capacity of 350 ml. The effluent gas is cooled to 20° C. (river water) and passed directly through a washer in order to hydrolyze unconverted phosgene.

Following subsequent reaction in a secondary reactor (SR) at 40° to 65° C., the acid chloride and catalyst phases are separated at room temperature in a phase separator, after which the composition of the acid chloride and the content of phosgene in the catalyst are determined. In all cases, the discharged material is free from phosgene.

The results are listed in Table 1 below.

TABLE 1

| Ex. | Acid | Catalyst | Temp. MR (°C.) | Temp. SR (°C.) | Acid chloride calc. purity (%) | Acid chloride content (%) | Phosgene content* of catalyst before (% molar) | Phosgene content* of catalyst after (% molar) | Phosgene loss (%) |
|---|---|---|---|---|---|---|---|---|---|
| 1 | Propionic acid | N,N-dimethyl formamide | 40 | 40 | 73 | 96.4 | 60 | 43 | 3.4 |
| 2 | Pivalic acid | N,N-dimethyl formamide | 50 | 50 | 94 | 98.0 | 60 | 50 | 2.0 |
| 3 | 2-Ethylhexanoic acid | N,N-dimethyl formamide | 50 | 50 | 99 | 99.5 | 50 | 44 | 1.2 |

TABLE 1-continued

| | | | Temp. | | Acid chloride | | Phosgene content* of catalyst | | |
|---|---|---|---|---|---|---|---|---|---|
| | | | MR | SR | calc. purity | content | before | after | Phosgene loss |
| Ex. | Acid | Catalyst | (°C.) | (°C.) | (%) | (%) | (% molar) | | (%) |
| 4 | Stearic acid | N,N-dimethyl formamide | 70 | 65 | 99 | 99.5 | 50 | 38 | 2.4 |
| 5 | Pivalic acid | N,N-diethyl formamide | 60 | 60 | 90 | 95.1 | 60 | 49 | 2.2 |
| 6 | 2-Ethylhexanoic acid | N,N-diethyl formamide | 60 | 60 | 98 | 99.5 | 50 | 42 | 1.6 |
| 7 | 2-Ethylhexanoic acid | N-formyl piperidine | 50 | 50 | 98 | 99.0 | 50 | 41 | 1.8 |
| 8 | Isobutyric acid** | N,N-dimethyl formamide | 45 | 50 | 97 | 98.5 | 50 | 45 | 1.0 |

*based on formamide
**off-gas cooled with brine at −15° C.

COMPARATIVE EXAMPLES 9 TO 14 Batch Phosgenation as per DE-A 3,836,987

2 Moles of a carboxylic acid and 0.4 mole of an N,N-disubstituted formamide are placed in a reactor having a capacity of 1 liter, and 238 g (2.4 moles) of phosgene are bubbled through the mixture at a temperature of from 50° to 70° C. over a period of 2 hours. The off-gas, after it has been cooled to 20° C. (river water), is passed directly through a washer in which unconverted phosgene is hydrolyzed.

On conclusion of the phosgene feed, the mixture is stirred for another 30 minutes before it is cooled to room temperature and passed to a separating funnel. After 0.5 h at 25° C., the discharged batch is separated into acid chloride and catalyst phases. In each case, the resulting batch is free from phosgene.

The results are listed in Table 2 below.

EXAMPLES 15 TO 21 Catalyst Recycle

At a temperature of from 40° to 70° C., 1 to 2 moles/h of a carboxylic acid containing 20% molar of adduct of phosgene and N,N-disubstituted formamide (phosgene content 50 to 60% molar, based on formamide) are introduced to a main reactor (MR) having a capacity of 350 ml together with sufficient phosgene to ensure that not only the phosgene converted to acid chloride but also that lost with the off-gases is compensated for. The off-gases are brine-cooled to −20° C.

Following subsequent reaction in a secondary reactor (SR) at 40° to 65° C., the acid chloride and catalyst phases are separated at room temperature in a phase separator. The catalyst, after replenishment with N,N-disubstituted formamide to make up for that removed with the acid chloride solution, is recycled. In all cases, the discharged material is free from phosgene.

TABLE 2

| | | | | Acid chloride | | | |
|---|---|---|---|---|---|---|---|
| Ex. | Acid | Catalyst | Temp. (°C.) | calc. purity (%) | content (%) | Phosgene content* of catalyst (% molar) | Phosgene loss (%) |
| 9 | 2-Ethylhexanoic acid | N,N-dimethyl formamide | 50 | 95 | 99.3 | 54 | 7.7 |
| 10 | Pivalic acid | N,N-diethyl formamide | 50 | 91 | 95.1 | 49 | 8.5 |
| 11 | 2-Ethylhexanoic acid | N,N-diethyl formamide | 60 | 97 | 99.1 | 60 | 6.9 |
| 12 | Stearic acid | N,N-diethyl formamide | 70 | 96 | 97.0 | 49 | 8.5 |
| 13 | Pivalic acid | N-formyl piperidine | 60 | 92 | 98.1 | 58 | 7.1 |
| 14 | 2-Ethylhexanoic acid | N-formyl piperidine | 60–70 | 98 | 99.2 | 72 | 4.7 |

*based on formamide moiety

The results are listed in Table 3 below.

TABLE 3

| | | Moles/ | | Phosgene content of catalyst (% molar, | Temp. (°C.) | | Phosgene | Recycle | Final product (area %) | | Phosgene loss |
|---|---|---|---|---|---|---|---|---|---|---|---|
| Ex. | Acid | h | Cat. | based on formamide) | MR | SR | (moles/h) | stage | Acid chloride | Formamide | (%) |
| 15 | Propionic acid | 1.20 | DMF[a] | 60 | 40 | 40 | 1.25 | 1 | 97.2 | 1.1 | 4.0 |
| | | 1.10 | | | | | 1.13 | 2 | 96.4 | 1.5 | 2.7 |
| 16 | isobutyric acid | 1.00 | DMF[a] | 55 | 45 | 50 | 1.01 | 1 | 98.8 | 0.6 | 1.0 |
| | | 1.50 | | | | | 1.52 | 2 | 98.5 | 0.7 | 1.3 |
| | | 2.00 | | | | | 2.04 | 3 | 98.1 | 0.8 | 1.9 |
| | | 2.00 | | | 40 | 45 | 2.05 | 4 | 98.8 | 0.8 | 2.4 |
| | | 2.00 | | | 45 | 20 | 2.05 | 5 | 98.1 | 0.5 | 2.4 |
| 17 | 2-Ethylhexanoic acid | 1.30 | DMF[a] | 50 | 50 | 50 | 1.32 | 1 | 99.4 | 0.1 | 1.5 |
| | | | | | | | | 2 | 99.5 | 0.2 | 1.5 |
| | | | | | | | | 3 | 99.7 | 0.1 | 1.5 |
| 18 | Pivalic acid | 1.40 | DMF[a] | 50 | 50 | 50 | 1.42 | 1 | 98.6 | 0.3 | 1.5 |
| | | | | | | | 1.43 | 2 | 99.1 | 0.6 | 2.1 |
| 19 | Stearic acid | 0.80 | DMF[a] | 45 | 70 | 60 | 0.82 | 1 | 99.5 | 0.1 | 2.4 |
| | | 1.00 | | | | | 1.03 | 2 | 99.4 | 0.1 | 2.9 |
| 20 | Pivalic acid | 1.70 | DEF[b] | 60 | 60 | 60 | 1.75 | 1 | 95.1 | 2.5 | 2.8 |

TABLE 3-continued

| Ex. | Acid | Moles/h | Cat. | Phosgene content of catalyst (% molar, based on formamide) | Temp. (°C.) MR | Temp. (°C.) SR | Phosgene (moles/h) | Recycle stage | Final product (area %) Acid chloride | Final product (area %) Formamide | Phosgene loss (%) |
|---|---|---|---|---|---|---|---|---|---|---|---|
| 21 | 2-Ethylhexanoic acid | 1.30 | DEF[b] | 50 | 60 | 60 | 1.75 | 2 | 94.5 | 3.2 | 2.8 |
|  |  |  |  |  |  |  | 1.32 | 1 | 97.8 | 1.1 | 1.5 |
|  |  |  |  |  |  |  | 1.32 | 2 | 97.4 | 1.3 | 1.5 |
|  |  |  |  |  |  |  | 1.33 | 3 | 97.5 | 1.3 | 2.2 |

[a] DMF  N,N-dimethyl formamide
[b] DEF  N,N-diethyl formamide

I claim:

1. In a process for the preparation of a carboxylic chloride of the formula

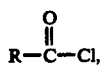

$$R-\overset{O}{\underset{\|}{C}}-Cl, \quad (I)$$

in which R denotes $C_1$–$C_{30}$-alkyl, $C_2$–$C_{30}$-alkenyl or $C_2$–$C_{30}$-alkynyl, by reacting a carboxylic acid of the formula

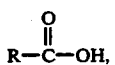

$$R-\overset{O}{\underset{\|}{C}}-OH, \quad (II)$$

in which R has the meanings stated with liquid or gaseous phosgene

$$COCl_2, \quad (III)$$

in the presence of a catalyst adduct of phosgene and N,N-disubstituted formamide of the formula

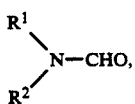

$$\begin{array}{c} R^1 \\ \phantom{R^1}\diagdown \\ \phantom{RRR}N-CHO, \\ \phantom{R^1}\diagup \\ R^2 \end{array} \quad (IV)$$

in which $R^1$ and $R^2$ are independently $C_1$–$C_3$-alkyl or $R^1$ and $R^2$ together form a $C_4$- or $C_5$-alkylene chain which may or may not be interrupted by an oxygen atom or by a nitrogen atom carrying a $C_1$–$C_3$-alkyl group or CHO, the product (I) being isolated from the catalyst adduct by phase separation, the improvement which comprises:

carrying out the reaction in the presence of said catalyst adduct of phosgene and N,N-disubstituted formamide (IV) in which the amount of phosgene in the adduct is kept between about 20 to 70% molar, based on the formamide.

2. A process as claimed in claim 1, wherein the reaction is carried out continuously.

3. A process as claimed in claim 1, wherein the amount of phosgene in the catalyst adduct is kept between about 30 to 60% molar, based on the formamide.

4. A process as claimed in claim 1, wherein the amount of phosgene in the catalyst adduct is kept between about 40 to 50% molar, based on the formamide.

5. A process as claimed in claim 1, wherein the carboxylic acid reactant (I) is an aliphatic monocarboxylic acid of from 1 to 30 carbon atoms.

6. A process as claimed in claim 1, wherein the carboxylic acid reactant (I) is an aliphatic monocarboxylic acid of from 1 to 20 carbon atoms.

7. A process as claimed in claim 1, wherein the reaction of the carboxylic acid (II) and the phosgene (III) is carried out at a temperature between 20° and 100° C.

8. A process as claimed in claim 1, wherein the reaction of the carboxylic acid (II) and the phosgene (III) is carried out at a temperature between 30° and 80° C.

9. A process as claimed in claim 1, wherein the reaction of the carboxylic acid (II) and the phosgene (III) is carried out at a temperature between 40° and 70° C.

10. A process as claimed in claim 1, wherein the catalyst adduct of phosgene and the N,N-disubstituted formamide (IV) is used in an amount of from 5 to 200% molar, based on the carboxylic acid reactant (II).

11. A process as claimed in claim 1, wherein the catalyst adduct of phosgene and the N,N-disubstituted formamide (IV) is used in an amount of from 10 to 100% molar, based on the carboxylic acid reactant (II).

12. A process as claimed in claim 1, wherein the catalyst adduct of phosgene and the N,N-disubstituted formamide (IV) is used in an amount of from 10 to 30% molar, based on the carboxylic acid reactant (II).

13. A process as claimed in claim 1, wherein the formamide (IV) in the catalyst adduct is selected from the group consisting of dimethyl formamide and diethyl formamide.

* * * * *